(12) United States Patent
Shanklin

(10) Patent No.: US 7,488,695 B2
(45) Date of Patent: Feb. 10, 2009

(54) ANTIMICROBIAL ABSORBENT ARTICLE, AND METHODS OF MAKING AND USING THE SAME

(75) Inventor: Gary L. Shanklin, Fremont, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 302 days.

(21) Appl. No.: 11/546,125

(22) Filed: Oct. 10, 2006

(65) Prior Publication Data

US 2007/0032154 A1    Feb. 8, 2007

Related U.S. Application Data

(63) Continuation of application No. 09/753,134, filed on Dec. 29, 2000, now Pat. No. 7,132,379.

(60) Provisional application No. 60/174,088, filed on Dec. 30, 1999.

(51) Int. Cl.
*B32B 5/02* (2006.01)
*B32B 27/12* (2006.01)
*B32B 27/04* (2006.01)
*A61F 13/00* (2006.01)
*A61F 13/15* (2006.01)
*A61L 13/15* (2006.01)

(52) U.S. Cl. .................. 442/123; 442/97; 442/99; 442/102; 424/443; 424/447; 604/358

(58) Field of Classification Search .............. 442/123, 442/99, 97, 102; 424/443, 446, 447; 428/532, 428/537.1, 537.5; 604/358

See application file for complete search history.

(56) References Cited

U.S. PATENT DOCUMENTS

| | | | |
|---|---|---|---|
| 4,738,847 A | 4/1988 | Rothe et al. |
| 4,764,418 A | 8/1988 | Kuenn et al. |
| 4,790,836 A | 12/1988 | Brecher |
| 4,824,689 A | 4/1989 | Kuenn et al. |
| 4,828,912 A | 5/1989 | Hossain et al. |
| 4,857,334 A | 8/1989 | Korol et al. |
| 4,891,228 A | 1/1990 | Thaman et al. |
| 4,897,304 A | 1/1990 | Hossain et al. |
| 4,950,545 A | 8/1990 | Walter et al. |
| 5,006,339 A | 4/1991 | Bargery et al. |
| 5,059,282 A | 10/1991 | Ampulski et al. |
| 5,196,244 A | 3/1993 | Beck |

(Continued)

FOREIGN PATENT DOCUMENTS

WO    WO 99-37860    7/1999

*Primary Examiner*—Lynda Salvatore
(74) *Attorney, Agent, or Firm*—Brinks Hofer Gilson & Lione

(57) ABSTRACT

A non-irritating multi-ply absorbent article made by treating an inner surface with one or more antimicrobial agents and treating the one or more outer surfaces with one or more siloxane compositions, and methods of making and using the same. The antimicrobial agent will remain confined to the inner portion of the absorbent article, thereby preventing irritation to the user, and the siloxane treated ply(s) will provide a pleasing, soothing, non-irritating tactile quality. In one embodiment, the siloxane composition comprises an amine-modified polysiloxane, in which case the product will also entrap any absorbed fluid, holding it in contact with the antimicrobial agent, and preventing it from wetting through the product and contacting the user.

10 Claims, 2 Drawing Sheets

U.S. PATENT DOCUMENTS

| | | |
|---|---|---|
| 5,227,242 A | 7/1993 | Walter et al. |
| 5,362,482 A | 11/1994 | Yoneyama et al. |
| 5,567,372 A | 10/1996 | Nohr et al. |
| 5,580,566 A | 12/1996 | Syverson et al. |
| 5,635,191 A | 6/1997 | Roe et al. |
| 5,720,966 A | 2/1998 | Ostendorf |
| 5,830,487 A | 11/1998 | Klofta et al. |
| 5,849,311 A | 12/1998 | Sawan et al. |
| 5,888,524 A | 3/1999 | Cole |
| 5,888,526 A | 3/1999 | Tsubai et al. |
| 6,054,020 A | 4/2000 | Goulet et al. |
| 6,544,386 B1 | 4/2003 | Krzysik et al. |
| 2002/0001726 A1 | 1/2002 | Burghardt et al. |

ANTIMICROBIAL ABSORBENT ARTICLE, AND METHODS OF MAKING AND USING THE SAME

RELATED APPLICATIONS

This application is a continuation of U.S. application Ser. No. 09/753,134 entitled "Antimicrobial Absorbent Article, and Methods of Making and Using the Same," filed Dec. 29, 2000 now U.S. Pat. No. 7,132,379, which is a continuation of U.S. application Ser. No. 60/174,088, filed on Dec. 30, 1999, the entire disclosures of which are incorporated herein by reference.

FIELD OF THE INVENTION

The present invention generally relates to an absorbent article such as a facial tissue which comprises several plies or plies of material. More particularly, the present invention relates to a multi-ply absorbent article and methods of making and using the same wherein one or more inner surfaces of one or more plies is treated with an antimicrobial agent, and one or more outer surfaces of one or more plies is treated with a siloxane composition.

BACKGROUND

Antimicrobial articles treated with virucides and germicides are known in the art. U.S. Pat. Nos. 4,828,912 and 4,897,304, both issued to Hossain et al., pertain to the use of a carboxylic acid/surfactant virucidal composition in absorbent products. U.S. Patent Nos. 4,764,418 and 4,824,689, both issued to Kuenn et al., pertain to the addition of water-soluble humectants to carboxylic acid/surfactant virucides for use in tissue products to reduce irritation potential. U.S. Pat. No. 4,738,847 issued to Rothe et al., pertains to adding a carboxylic acid/surfactant virucide to the center ply of a three ply tissue to prevent transfer of the virucidal composition to the user, and thereby reduce irritation potential.

Products such as those disclosed in the Hossain et al. and Kuenn et al. patents can be highly irritating because the virucidal carboxylic acids come in contact with the skin when the tissue is used. There is also no mechanism for preventing the body secretion or fluid from soaking through the tissue and contacting the user.

Products such as those of Rothe et al. have less potential for irritation because the virucidal composition is confined in the inner ply. However, these tissues tend to be harsh rather than soft because the water added with the virucidal composition degrades the tactile properties of the tissue. There is also no mechanism for preventing the body secretion or fluid from soaking through the tissue and contacting the user.

Irritation caused by virucidal or germicidal treatments to absorbent articles is a persistent problem. There have been attempts to ameliorate this problem by mixing the virucidal or germicidal treatment with lotions or emollients. U.S. Pat. No. 5,720,966 issued to Ostendorf, pertains to a "medicated" lotion absorbent article. The "medication" may be a virucide or disinfectant. U.S. Pat. No. 5,830,487 issued to Klofta et al. pertains to a tissue with a virucidal lotion. The lotion comprises a carboxylic acid/nonionic surfactant virucidal composition. In both the Ostendorf and Klofta, et al. patents, the intent is for the lotion to reside predominantly on the surface of the absorbent article and transfer to the user.

Products such as those disclosed in the Ostendorf and Klofta et al. patents also have a high potential for irritation because the virucidal or germicidal composition is on the surface of the tissue and is intentionally transferred to the user, so the user remains in prolonged contact with the irritant. There is also no mechanism for preventing the body secretion or fluid from soaking through the tissue and contacting the user.

Siloxane treated tissues are also known in the art. U.S. Pat. No. 5,227,242 issued to Walter et al., and U.S. Pat. No. 5,059,282 issued to Ampulski et al., each pertain to a tissue treated with a siloxane composition resulting in a tissue that is soft, absorbent, and leaves a low amount of residue.

Prior art products such as those of Walter et al. and Ampulski et al. are very soft. However, they do nothing to kill or inactivate any microorganisms that may be present, so the discarded products remain a breeding ground and reservoir of potentially harmful microorganisms that may contribute to the spread of disease.

SUMMARY

The present invention provides an absorbent article that is soft, non-irritating, and capable of killing microorganisms. More specifically, the present invention provides a multi-ply absorbent article having an outer ply treated with a siloxane composition and an inner surface treated with an antimicrobial agent.

In one aspect of the invention, the absorbent article includes a plurality of plies, at least one of the plies defining an outer ply; at least one of the plies having a surface defining an inner surface; one or more siloxane compositions applied to the at least one outer ply; and an antimicrobial effective amount of one or more antimicrobial agents applied to the at least one inner surface.

In a further aspect of the invention, a method is provided for making the multi-ply absorbent article. In yet another aspect of the invention, a method is provided for using the multi-ply absorbent article to inhibit the spread of illness.

Other aspects of the invention will be apparent in view of the following description of the preferred embodiments and the accompanying drawings.

DETAILED DESCRIPTION OF THE PREFERRED EMBODIMENTS

Figure 1:
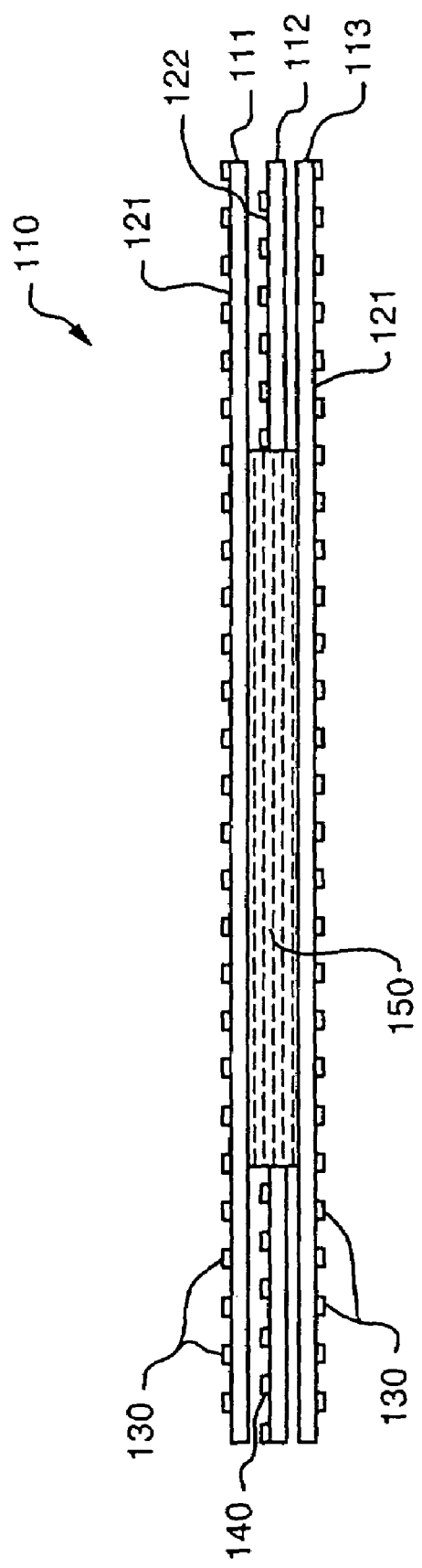
FIG. 1 is a diagram of an absorbent article having three plies, including two outer plies, according to one embodiment of the invention.

Referring now to the accompanying drawings and initially to FIG. 1, a multi-ply absorbent product is shown generally at 110. The term "plies" refers to discrete product elements arranged in juxtaposition to each other. The term may refer to a plurality of web-like components such as in a multi-ply facial tissue; or it may refer to a collection of functional components arranged into a functional product, such as the liner, wrap sheet, absorbent, outer cover, etc., of diapers or other personal care products. The term "layer" refers to a plurality of strata of different fibers, chemical treatments, etc., within a ply.

In the embodiment shown in FIG. 1, the multi-ply absorbent article 110 has a first outer ply 111, an inner ply 112, and a second outer ply 113. The first outer ply 111 and the second outer ply 113 each have an outwardly facing surface defining outer surfaces 121. At least one surface of the inner ply 112 defines an inner surface 122. In the embodiment shown, only one of the surfaces of the inner ply 112 defines an inner surface 122; however, those skilled in the art will appreciate that in other embodiments both surfaces of the inner ply 112 may define an inner surface.

The plies of the absorbent article may be made from a cellulosic web, and formed as a three-ply facial tissue, bath tissue, paper towel, and the like. Alternately, the plies may be suitable nonwoven substrates and formed into articles such as industrial wipes, wet wipe materials such as wet-creped hand towels and spunbonded and meltblown polymeric webs commonly used in production of disposable hospital items such as surgical drapes, gowns, bedsheets, pillowcases, and the like. Other examples of nonwovens include composites of natural and/or synthetic fibers, formed by turbulent admixing, in nonwoven form. Textile materials of all types, including laminates of different materials, may be used as suitable substrates. For example, hygienic face masks used by persons suffering from respiratory illnesses provide an excellent means for utilizing the present invention. Other essentially inert carriers i.e., those which are essentially non-toxic and non-irritating to human or animal tissue under the conditions of normal use, will be apparent to those skilled in the art.

The inner surface(s) 122 of inner ply 112 is treated with an antimicrobial effective amount of an antimicrobial agent 140. The term "antimicrobial effective amount" as used herein means an amount of an antimicrobial agent is effective to reduce the rate at which targeted microbes reproduce or to reduce the population of the microbes.

The antimicrobial agent serves to kill or inactivate any microorganisms, such as viruses, bacteria, or fungi, that are absorbed into the tissue with body secretions or fluids, thereby inhibiting the spread of disease, such as a viral infection. In a preferred method of use of the multi-ply absorbent article to inhibit the spread of illness, the multi-ply absorbent article is a facial tissue. A user contacts the absorbent article with a bodily discharge, such as a nasal discharge, and entraps the bodily discharge against the anti-microbial agent. The antimicrobial agent is confined to the inner surfaces of the multi-ply absorbent article ply(s), thus preventing its transfer to the skin and resultant irritation.

At least one of the outer surfaces 121 of the outer plies 111 and 113 is treated with a siloxane composition 130, which gives the outer plies a softer feel. In a preferred embodiment, the siloxane compound 130 is an amine-modified polysiloxane. The amine-modified polysiloxanes of the siloxane composition 130 preferentially reside on the outer surface of the substrate to which they are applied, either as a result of hydrogen bonding, charge attraction, or other chemical interaction, thereby providing a softness benefit on the surface and providing a degree of water or fluid repellency. However, when a fluid does penetrate the outer surface, the fluid is readily absorbed by the central inner ply 112 and the polysiloxane on the opposite outer surface 113 delays further penetration of the liquid to the outside of the tissue, thus trapping the fluid 150 in the center of the product in contact with the antimicrobial agent. This "one-way-valve" effect protects the user from product wet-through during normal use, and entraps the fluid in contact with the antimicrobial agent.

The particulars of both the antimicrobial agent and the siloxane composition will be discussed in detail below.

Figure 2:
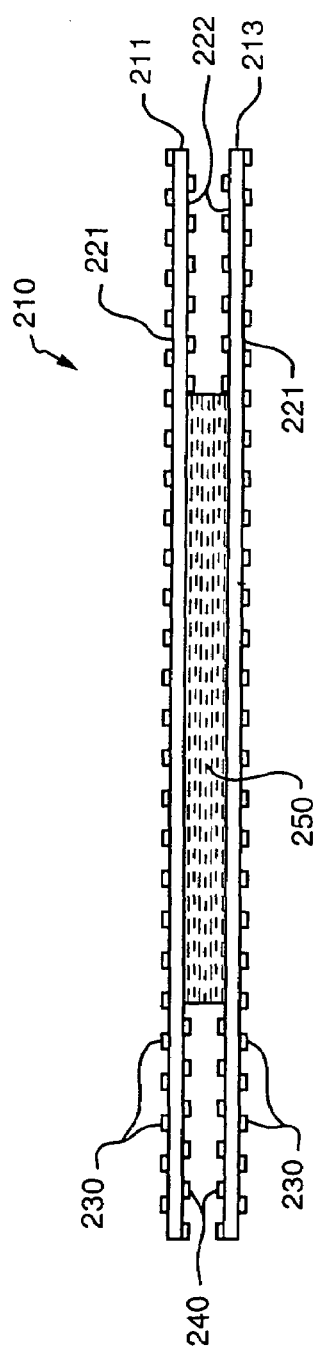
FIG. 2 is a diagram of an absorbent article having two plies according to a second embodiment of the invention.

FIG. 2 illustrates a second embodiment of the invention. The absorbent article 210 of this embodiment has two outer plies 211, 213. At least one of the outward surfaces 221 of the outer plies 211, 213 are treated with a siloxane compound 230. In this embodiment, there is no inner ply. The inner surface(s) 222 are defined by the inward surfaces of the outer plies 211, 213. At least one of the inner surface(s) 222 is treated with an antimicrobial agent 240. As in the first embodiment, when the siloxane compound is an amine-modified polysiloxane, entrapped fluid 250 in the center of the article is placed in contact with the antimicrobial agent, thus killing microorganisms within the fluid 250 and preventing further exposure to the user.

Figure 3:
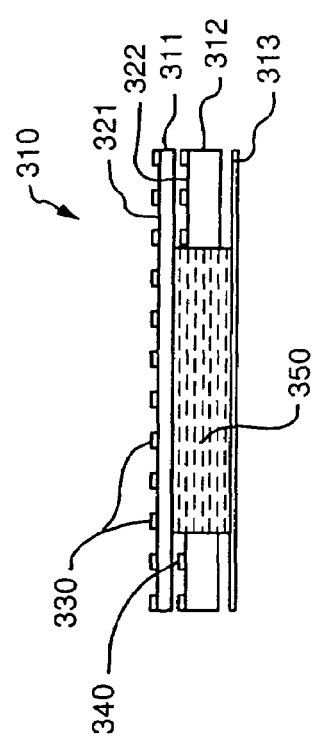
FIG. 3 is a diagram of an absorbent article having three plies, including an outer ply, an absorbent inner ply, and a liquid-impermeable-ply, according to a third embodiment of the invention.

FIG. 3 illustrates a third embodiment of the invention. The absorbent article 310 includes an outer ply 311, an inner absorbent ply 312, and a fluid or liquid impermeable base ply 313. This embodiment is especially useful for products such as diapers, incontinence pads, and sanitary napkins, and the plies are made from materials generally known in the art for those products.

The outer ply 311 is generally made from material(s) that are hydrophilic, compressible, conformable and non-irritating to the wearer's skin. Acceptable materials are well known in the art and include, for example, various natural or synthetic fibers, wood pulp fibers, regenerated cellulose or cotton fibers, or a blend of pulp and other fibers, meltblown polymer, such as polyester, and polypropylene.

The inner absorbent ply 312 may also be comprised of other well-known materials used in absorbent articles, including multiple plies of cellulose wadding, rayon fibers, cellulose sponge, hydrophilic synthetic sponge, such as polyurethane, and the like.

Preferred materials for base ply 313 include polyolefin films such as polyethylene and polypropylene; copolymers of polyolefins including, but not limited to, ethylene vinyl acrylate and ethylene acrylic; microporous fabrics and microporous or micro-apertured films such as Goretex® sold by the W. T. Gore Company of Flagstaff and Phoenix, Ariz.; "sized" papers, tissue or paper treated with amino-functional siloxanes.

The outward surface 321 of outer ply 311 is treated with a siloxane compound 330. At least one surface of the inner absorbent ply 312 defines an inner surface 322 and is treated with the antimicrobial agent 340.

As with the other embodiments, the outer ply 311, when treated with an amine-modified polysiloxane, acts as a "one-way valve," entrapping fluid 350. The microorganisms in the entrapped fluid 350 are killed by the antimicrobial agent 340, thereby limiting the exposure of the product user to the microorganisms.

Antimicrobial Agent

The antimicrobial agent may comprise any of the virucides, bacteriocides, germicides, fungicides, and disinfectants known in the art. Selection of any particular agent will be dependent on its efficacy versus relevant microorganisms, human safety and toxicological profile, and environmental safety and toxicological profile.

Preferred antimicrobial agents are virucidal compositions. Especially preferred virucidal compositions include, without limitation, the carboxylic acid or the carboxylic acid/surfactant compositions disclosed in U.S. Pat. No. 4,897,304, issued to Hossain et al.; U.S. Pat. No. 4,764,418, issued to Kuenn et al.; and U.S. Pat. No. 4,738,847, issued to Rothe et al., all of which are incorporated herein by reference.

As used herein, an anti-viral carboxylic acid is a material that is capable of killing such viruses as rhinovirus and influenza. Carboxylic acids useful as virucides in the present invention include, without limitation, the compounds having the structure:

R—COOH wherein R is a radical selected from the group consisting of $C_1$-$C_6$ alkyl, substituted $C_1$-$C_6$ alkyl, carboxy $C_1$-$C_6$ alkyl, carboxyhydroxy $C_1$-$C_6$ alkyl, carboxy halo $C_1$-$C_6$ alkyl, carboxy dihydroxy $C_1$-$C_6$ alkyl, dicarboxyhydroxy $C_1$-$C_6$ alkyl, $C_1$-$C_6$ alkenyl, carboxy $C_1$-$C_6$ alkenyl, dicarboxy $C_1$-$C_6$ alkenyl, phenyl, and substituted phenyl radicals. The hydrogen atoms of any of the above compounds may be substituted by one or more functional groups such as halogen atoms, hydroxyl groups, amino groups, thiol groups, nitro groups, and cyano groups, etc.

Especially preferred acids include citric acid, malic acid, maelic acid, tartaric acid, salicylic acid, glycolic acid, adipic acid, glutaric acid, succinic acid, benzoic, and mixtures thereof.

The carboxylic acids can be present in the tissue product in any amount which is virucidally effective. The term "virucidally effective amount" means an amount sufficient to cause a 2 log drop in rhinovirus type 16 within 20 minutes in accordance with the Virucidal Assay Test described in the abovesaid U.S. Pat. No. 4,897,304 and Canadian Patent No. 1,188, 225, although those skilled in the art of virology will recognize other suitable test procedures for this purpose. The addition rate on the virucidal composition to the tissue surface is preferred to be about 0.5 to 5.0 mg/in$^2$.

The carboxylic acids may be combined with a surfactant. Carboxylic acid/surfactant virucides are effective at add-on rates as low as 0.5 mg/in$^2$. The surfactant may be cationic, anionic, or nonionic. Preferred nonionic surfactants include the polyoxyethylenated alkylphenols such as TRITON X-100®, manufactured by Union Carbide of Danbury, Conn., and the polyoxyethylenated sorbitol esters such as TWEEN 40®, manufactured by Uniquiema of Wilmington, Del. Preferred cationic surfactants include cetylpyridinium chloride ($C_5H_5N^+(CH_2)_{15}$ $CH_3Cl^-$), dimethylbenzethonium quaternary ammonium chloride ($Me_3CCH_2C(Me)_2C_6H_3(Me)$-$OCH_2$ $CH_2$ $OCH_2CH_2{}^+N(Me)_2H_2C_6H_5Cl^-$). The preferred anionic surfactants may be represented by the structures:

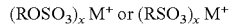
$(ROSO_3)_x\ M^+$ or $(RSO_3)_x\ M^+$ wherein, M$^+$ is a mono, di or trivalent metal cation or an ammonium or substituted ammonium ion; x is an integer; and R is an alkyl group; or

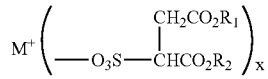
$$M^+ \begin{pmatrix} & CH_2CO_2R_1 \\ —O_3S— & CHCO_2R_2 \end{pmatrix}_x$$

wherein, M$^+$ and x are defined as above and $R_1$ and $R_2$ may be the same or different and may be represented by straight or branched chain aliphatic groups.

Preferred anionic surfactants include secondary alkane sulfonates and sarcosinate surfactants. Especially preferred anionic surfactants include sodium dodecyl sulfate ($CH_3$ $(CH_2)_{10}$—$CH_2$ $OSO_3$—Na), and the 1,4-bis(2-ethylhexyl)ester, sodium salt of sulfosuccinic acid, as manufactured by Cytec Industries of West Paterson, N.J., under the tradename of AEROSOL OT. The above surfactants are presented in an illustrative rather than a limiting sense.

Other additives may also be added to the anti-viral carboxylic acid. In a preferred embodiment, the antimicrobial agent includes a water-soluble humectant. For purposes herein, the term "humectant" means a hygroscopic compound or material which has an affinity for water and acts to stabilize the moisture content of a cellulosic web in the presence of fluctuating humidity. The term "water-soluble" means having a Hydrophile-Lipophile Balance (HLB) number of 7 or greater. The HLB index is well known in the chemical arts and is a scale which measures the balance between the hydrophilic and lipophilic solution tendencies of a compound. The HLB scale ranges from 1 to approximately 50, with the lower numbers representing highly lipophilic tendencies and the higher numbers representing highly hydrophilic tendencies. The presence of a water-soluble humectant can inhibit age-induced reduction in softness in webs containing carboxylic acids, particularly under conditions of low humidity (less than 35% relative humidity).

The water-soluble humectant can be any such material or compound which can be applied to the tissue web in a uniform manner, as by spraying, coating, dipping or printing, etc., and which possesses hygroscopic or humectant properties and which will not interfere with the virucidal effectiveness of the tissue product to the extent that the tissue product is no longer virucidally effective. It must be pointed out that many lotion-type tissue additives, which have HLB numbers less than 7 and hence are not water-soluble, interfere with virucidal activity. Examples of suitable water-soluble humectants include: polyglycols (as hereinafter defined), propylene glycol, sorbitol, lactic acid, sodium lactate, glycerol, and ethoxylated castor oil.

Polyglycols, which for purposes herein include esters or ethers of polyglycols, having a weight average molecular weight of from about 75 to about 90,000 are suitable for purposes of this invention. This molecular weight range represents physical states ranging from a low viscosity liquid to a soft wax to a fairly hard solid. The higher molecular weight polyglycols naturally have to be melted in order to be applied to a tissue web. Examples of suitable polyglycols include polyethylene glycol, polypropylene glycol, polyoxypropylene adducts of glycerol, methoxypolyethylene glycol, polyethylene glycol ethers of sorbitol, polyethylene glycol ethers of glycerol, polyethylene glycol ethers of stearic acid, polyethylene glycol ethers of lauryl alcohol, citric acid fatty esters, malic acid fatty esters, polyethylene glycol ethers of oleyl alcohol, and ethoxylated stearate esters of sorbitol. Polyethylene glycol is a preferred polyglycol because it can be applied to the tissue in amounts which are effective in improving softness without leaving a noticeable residue on the consumer's hands. Polypropylene glycol is also effective, but tends to leave more of a residue at equivalent amounts and is more hydrophobic than polyethylene glycol.

The amount of water-soluble humectant in a single ply or web of a tissue product of this invention can be about 0.05 to weight percent or greater. The weight percentage amount can vary greatly, depending upon the desired tactile properties, the amount of carboxylic acid present that needs to be counteracted, the properties of the water-soluble humectant itself, etc. Preferably, the amount of polyglycol in a single ply of the absorbent article can be from about 2 to about 6 weight percent.

The antimicrobial agent may comprise agents other than carboxylic acids. For example, in one embodiment, the antimicrobial agent comprises at least one quaternary ammonium compound. Preferred quaternary ammonium compounds include cetylpyridinium chloride, methylbenzethonium chloride, benzethonium chloride, benzalkonium chloride, n-alkyl dimethyl benzyl ammonium chlorides, and n-alkyl dimethylethylbenzyl ammonium chlorides. Especially preferred quaternary ammonium compounds include cetylpyridinium chloride, methylbenzethonium chloride, benzethonium chloride, benzalkonium chloride. In another preferred embodiment, the antimicrobial agent comprises triclosan. Those skilled in the art will appreciate that a wide range of antimicrobial agents can be useful in the present invention, and the selection of a particular antimicrobial agent will depend upon the characteristics of a particular fluid that the particular absorbent article is designed to entrap.

Siloxane Composition

The siloxane composition serves to soften the tissue and contributes to a pleasing, smooth, soothing, non-irritating tactile quality. Particular siloxane compositions can be tailored to enhance the absorbency characteristics of the absorbent article, such as by inhibiting wet-through or by entrapping the secretions or fluids within the inner regions of the absorbent article.

Suitable siloxane compositions include, but are not limited to, polydimethyl siloxanes, silicone glycols, epoxyfunctional silicones, carboxyfunctional silicones, hydroxyfunctional silicones, other organofunctional silicones, amine functional silicones, cationic silicones, silicone betaines, silicone amidoamine esters, silicone amidoamine phosphates, and mixtures thereof.

Especially preferred siloxanes are amine-modified polysiloxanes, such as those disclosed in commonly assigned copending U.S. Ser. No. 09/012,588, "Soft Absorbent Tissue Products Having Delayed Moisture Penetration," filed Jan. 23, 1998, and incorporated herein by reference.

Amine-modified polysiloxane materials which are suitable for purposes of this invention have the following general formula:

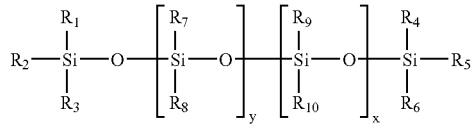

wherein x and y are integers >0. The mole ratio of x to (x+y) can be from 0.005 percent to about 25 percent. The $R_1$-$R_9$ moieties are selected from $C_1$ to $C_6$ alkyl substituents. Additionally, $R_2$ and $R_5$ are selected from hydroxyl or $C_1$ to $C_6$ alkyl alcohol substituents. Preferred $R_1$-$R_9$ moieties include $C_1$-$C_4$.

The $R_{10}$ moiety includes at least one amine-related functional group or groups such as amine, imine, and/or amide. For example, the amine-modified polysiloxane can be a polysiloxane where the $R_{10}$ moiety contains one amine group per substituent or two or more amine groups per substituent, separated by a linear or branched alkyl chain.

Modified polysiloxane materials which are suitable for blending or mixing with the amine-modified polysiloxane(s) for purposes of balancing the hydrophobicity in accordance with this invention have the following general formula:

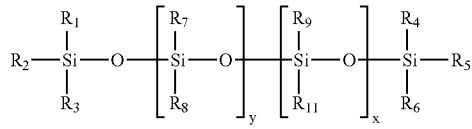

wherein x and y integers >0. The mole ratio of x to (x+y) can be from 0.005 percent to about 25 percent. The $R_1$-$R_9$ moieties are selected from $C_1$ to $C_6$ alkyl substituents. Additionally, $R_2$ and $R_5$ are selected from hydroxyl or $C_1$ t0 $C_6$ alkyl alcohol substituents.

Preferred $R_1$-$R_9$ moieties include $C_1$-$C_4$. The $R_{11}$ moiety includes at least one organic functional groups such as ethers, plyethers, esters, amines, imines, amides, or other functional groups, including the alkyl and alkenyl analogues of such functional groups.

As an example, the $R_{11}$ moiety can be a polyether functional group of the generic form —$R_{12}$—$(R_{13}$-0$)_a$-$(R_{14}$-0$)_b$-$R_{15}$; wherein $R_{12}$; $R_{13}$ and $R_{14}$ are alkyl chains of $C_1$ to $C_3$, $R_{15}$ can be hydrogen or a $C_1$-$C_4$ alkyl group, and "a" and "b" can be integers of from 1-100, more specifically from 10-30.

The viscosity range of the amine-modified polysiloxane, which is indicative of the molecular weight, can be from about 25 centipoise to about 2,000,000 centipoise or higher, more specifically from about 100 to about 1,000,000 centipoise.

In order to further optimize and balance the softness, hand protection and absorbency benefits of the modified polysiloxane treatment, blends of two or more modified polysiloxane materials can be applied to the surface of the tissue. In one particular example, a blend of a hydrophobic amino-modified polysiloxane and a hydrophilic polyether-modified polysiloxane can be used. The ratio of the amino-modified polysiloxane to the polyether-modified polysiloxane can be form 100 percent to about 10 percent, and more specifically from 100 percent to about 50 percent.

Those familiar with the polymer art will appreciate that the molecular weight (viscosity), the degree of substitution, the selected species for the various R groups and their chain lengths, the mole ratio of the "x" and "y" components of a single modified polysiloxane species, and blending two or more modified polysiloxane species can be varied to affect the hydrophobicity of the modified polysiloxane to be applied to the surface of the absorbent article.

The preferred addition rate of the siloxane composition is about 1%-2% siloxane solids per outer ply. An especially preferred add-on rate is about 1.5% siloxane solids per outer ply.

PROJECTION

In another aspect of the invention, a method of making a multi-ply absorbent article is provided. To produce the envisioned multi-ply absorbent article, it is necessary to treat an inner surface with the antimicrobial agent, ply the product together, and then crimp or seal the plies together before treating the outer plies or ply with the siloxane composition. This necessary because the sheet will become difficult to crimp or seal after the siloxane composition has been applied.

the antimicrobial agent may be applied to the center ply(s) by any of the means known in the art. Suitable means include spraying, foam application, electrostatic application, flexographic printing, and gravure printing. An especially preferred application method is smooth-roll coating. Other especially preferred methods include the gravure printing methods as disclosed in commonly assigned copending U.S. Ser. No. 60/174,087, entitled "Germicidal Tissue Product Using Rotogravure Rolls," filed Dec. 30, 1999; in U.S. Pat. No. 4,950,545 issued to Walter et al.; or in commonly assigned co-pending U.S. Ser. No. 09/012,588, "Soft Absorbent Tissue Products Having Delayed Moisture Penetration," filed Jan. 23, 1998, all of which are incorporated herein by reference.

Likewise, the siloxane composition may be applied to the outer plies by any of the means known in the art. Suitable means include spraying, foam application, electrostatic application, and flexographic printing. Especially preferred application methods are gravure or rotogravure printing. Gravure printing is preferred because of the control it offers with respect to the amounts added to the article surface. The amount of modified polysiloxane(s) applied to the surface of the absorbent article will depend on the particular modified polysiloxane. However, suitable add-on amounts are from about 0.1 to about 5 weight percent based on the dry weight of the tissue product, more specifically from about 0.5 to about 3 weight percent, and still more specifically from about 0.7 to about 2 weight percent. It is preferable to first emulsify the modified polysiloxane(s) in water using the appropriate surfactant before applying the emulsion to the surface of the absorbent article. While the modified polysiloxane(s) preferentially resides on the surface of the absorbent article to which it is applied, polysiloxanes inherently migrate such that even the center ply of a three-ply tissue product may contain some of the silicone material. However, such amounts are much less than the amount on the outer surface of the absorbent article so that the center ply remains substantially hydrophilic and can wick and absorb liquid.

The invention will be further illustrated with reference to the following specific example. It is understood that the example is given by way of illustration and is not meant to limit the disclosure or the claims that follow.

EXAMPLE

A virucidal tissue product was formed from three plies. An inner ply was treated with 1.5 mg/in$^2$ of a virucidal formulation comprising a 2:1 ratio of citric to malic acid. Two outer plies were treated on their outfacing surfaces with about 1.5% by weight of an amine-modified polysiloxane. The inner ply was then sandwiched between the outer plies. A control tissue product was also formed from three plies. All the plies in the control tissue product were untreated.

A 1.8×1.1 inch rectangular portion each of the virucide treated tissue and the untreated tissue were inoculated with rhinovirus 2, ATCC VR-482 test virus. After 15 seconds of virus exposure, the virucide on the treated tissue was rapidly neutralized and the amount of surviving test virus was determined in each tissue. The virucide/amine-modified polysiloxane tissue exhibited a 3.6 log reduction in viable test virus compared to the untreated control tissue.

It should be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention.

Accordingly, while the present invention has been described herein in detail in relation to several embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

The invention claimed is:

1. A method for inhibiting the transfer of illness comprising:
providing a multi-ply absorbent article comprising a plurality of plies, at least one of said plies defining an outer ply; at least one of said plies having a surface defining an inner surface; at least one siloxane composition applied to at least a portion of said at least one outer ply; and an antimicrobially effective amount of at least one antimicrobial agent applied to said at least one inner surface;
contacting a fluid containing microbes with said absorbent article;
absorbing said fluid within said absorbent article; and
entrapping said fluid in contact with said antimicrobial agent within said absorbent article;
wherein said at least one siloxane composition comprises at least one amine-modified polysiloxane selected from the group consisting of compounds having the formula:

$$R_2-\underset{R_3}{\underset{|}{\overset{R_1}{\overset{|}{Si}}}}-O-\left[\underset{R_8}{\underset{|}{\overset{R_7}{\overset{|}{Si}}}}-O\right]_y-\left[\underset{R_{10}}{\underset{|}{\overset{R_9}{\overset{|}{Si}}}}-O\right]_x-\underset{R_6}{\underset{|}{\overset{R_4}{\overset{|}{Si}}}}-R_5$$

wherein x and y are integers >0;
the mole ratio of x to (x+y) is from 0.005 percent to about 25 percent;
$R_1$, $R_3$, $R_4$, and $R_6$-$R_9$ are $C_1$ to $C_6$ alkyl substituents;
$R_2$ and $R_5$ are $C_1$ to $C_6$ alkyl, alkyl alcohol, or hydroxyl substituents; and
$R_{10}$ is a moiety including at least one functional group selected from the group consisting of amines, imines, and amides.

2. The method of claim 1, wherein said fluid is a nasal discharge.

3. The method of claim 1, wherein said illness is a viral infection.

4. The method of claim 1, wherein said antimicrobial agent comprises at least one virucide.

5. The method of claim 1, wherein said at least one siloxane composition comprises at least one amine-modified polysiloxane.

6. A method for making an antimicrobial, multi-ply absorbent article comprising:
applying an antimicrobially effective amount of at least one antimicrobial agent to at least one surface of a first tissue paper web;
applying an untreated tissue web to each surface of said first tissue paper web;
crimping said tissue paper webs together to form a three ply composite; and
applying at least one siloxane composition to at least one outer surface of said composite;
wherein said at least one siloxane composition comprises at least one amine-modified polysiloxane selected from the group consisting of compounds having the formula:

$$R_2-\underset{R_3}{\underset{|}{\overset{R_1}{\overset{|}{Si}}}}-O-\left[\underset{R_8}{\underset{|}{\overset{R_7}{\overset{|}{Si}}}}-O\right]_y-\left[\underset{R_{10}}{\underset{|}{\overset{R_9}{\overset{|}{Si}}}}-O\right]_x-\underset{R_6}{\underset{|}{\overset{R_4}{\overset{|}{Si}}}}-R_5$$

wherein x and y are integers >0;

the mole ratio of x to (x+y) is from 0.005 percent to about 25 percent;

$R_1$, $R_3$, $R_4$, and $R_6$-$R_9$ are $C_1$ to $C_6$ alkyl substituents;

$R_2$ and $R_5$ are $C_1$ to $C_6$ alkyl, alkyl alcohol, or hydroxyl substituents; and $R_{10}$ is a moiety including at least one functional group selected from the group consisting of amines, imines, and amides.

7. The method of claim 6, wherein said antimicrobial agent comprises at least one virucide.

8. A method for making an anti-microbial, multi-ply absorbent article comprising:

applying an antimicrobially effective amount of at least one antimicrobial agent to at least one surface of an absorbent material;

applying a liquid-impermeable base to one surface of said absorbent material;

applying a liquid-permeable outer ply to an opposite surface of said absorbent material;

assembling said absorbent material, said base, and said outer ply to form a three ply composite; and applying at least one siloxane composition to at least one surface of said outer ply;

wherein said at least one siloxane composition comprises at least one amine-modified polysiloxane selected from the group consisting of compounds having the formula:

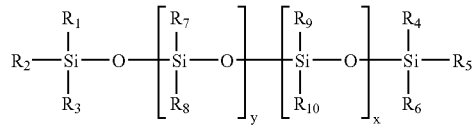

wherein x and y are integers >0;

the mole ratio of x to (x+y) is from 0.005 percent to about 25 percent;

$R_1$, $R_3$, $R_4$, and $R_6$-$R_9$ are $C_1$ to $C_6$ alkyl substituents;

$R_2$ and $R_5$ are $C_1$ to $C_6$ alkyl, alkyl alcohol, or hydroxyl substituents; and $R_{10}$ is a moiety including at least one functional group selected from the group consisting of amines, imines, and amides.

9. The method of claim 8, wherein said absorbent article is a diaper.

10. The method of claim 8, wherein said absorbent article is a sanitary napkin.

* * * * *